United States Patent
Horisberger et al.

(10) Patent No.: US 7,594,902 B2
(45) Date of Patent: Sep. 29, 2009

(54) CATHETER HEAD WITH CATHETER DRAIN IN DISCRETE ROTATIONAL POSITIONS

(75) Inventors: Ronny-Patrick Horisberger, Burgdorf (CH); Martin Wyss, Konolfingen (CH)

(73) Assignee: Disetronic Licensing AG, Burgdorf (CH)

( * ) Notice: Subject to any disclaimer, the term of this patent is extended or adjusted under 35 U.S.C. 154(b) by 502 days.

(21) Appl. No.: 10/889,360

(22) Filed: Jul. 12, 2004

(65) Prior Publication Data

US 2005/0020972 A1   Jan. 27, 2005

Related U.S. Application Data

(63) Continuation of application No. PCT/EP03/10179, filed on Sep. 12, 2003.

(30) Foreign Application Priority Data

Sep. 12, 2002   (DE) .............................. 102 42 419

(51) Int. Cl.
*A61M 31/00* (2006.01)
(52) U.S. Cl. ............ 604/93.01; 604/891.1; 604/288.01; 604/288.02; 604/288.03; 604/288.04
(58) Field of Classification Search ............. 604/890.1, 604/891.1, 93.01, 288.01–288.04, 164.01; 606/108, 167
See application file for complete search history.

(56) References Cited

U.S. PATENT DOCUMENTS

| 5,176,662 | A | 1/1993 | Bartholomew et al. |
| 5,968,011 | A | 10/1999 | Larsen et al. |
| 6,017,328 | A | 1/2000 | Fischell et al. |
| 6,736,797 | B1 * | 5/2004 | Larsen et al. .......... 604/167.05 |
| 2002/0123724 | A1 | 9/2002 | Douglas et al. |

FOREIGN PATENT DOCUMENTS

| DE | 201 14 795 U1 | 3/2002 |
| WO | WO 97/02848 | 1/1997 |
| WO | WO 00/03757 | 1/2000 |
| WO | WO 01/39818 A2 | 6/2001 |
| WO | WO 03/020343 A1 | 3/2003 |

* cited by examiner

*Primary Examiner*—Nicholas D Lucchesi
*Assistant Examiner*—Quynh-Nhu H Vu
(74) *Attorney, Agent, or Firm*—Dorsey & Whitney LLP

(57) ABSTRACT

A catheter head, for introduction of a fluid into an organic tissue, including a cannula housing with a cannula, a connector element with a fluid inlet, a guide and a fixing device. The guide device has several selectable discrete rotational positions for positioning the connector element relative to the cannula housing about a longitudinal axis of the cannula. The connector element, positioned in a rotational position, is detachably connected to the cannula housing in the selected position by means of the fixing device.

12 Claims, 2 Drawing Sheets

CATHETER HEAD WITH CATHETER DRAIN IN DISCRETE ROTATIONAL POSITIONS

CROSS-REFERENCE TO RELATED APPLICATIONS

This application is a Continuation of International Application No. PCT/EP2003/010179, filed on Sep. 12, 2003, which claims priority to German Application No. 102 42 419.5, filed on Sep. 12, 2002, the contents of both applications are incorporated in their entirety herein.

FIELD

The present invention relates to medical devices, including medical devices for transporting, transmitting, administering, extracting or delivering medicinal or other substances to and from other medical devices or patients. It also relates to methods of making and using such devices. More particularly, the present invention related to catheters and catheter heads, including a catheter head for introducing a fluid into an organic tissue, in particular a catheter head for administering a liquid active agent.

BACKGROUND

Catheter heads, including those of the type mentioned above, are, for example, used in conjunction with infusion means in order to enable a part of the catheter head—i.e., the cannula casing together with a cannula inserted in a body—to be changed or a fluid to be exchanged. This useful for a patient to whom a fluid is permanently or repeatedly administered. To this end, another part of the catheter head—the connecting element to a fluid supply—is detached from the cannula casing and, once the cannula casing has been exchanged, can be placed onto the new cannula casing attached to the body in order to continue introducing the fluid. At the same time, a new fluid container can easily be connected to the connecting element. It is also possible to place another, homogeneous connecting element of a new fluid container onto the cannula casing, such that the fluid can continue to be administered. Such a catheter head can however also be used for example to remove analysis liquid from a patient's body or to introduce the analysis liquid into the body and remove it again.

In general, the cannula casing of the catheter head comprises a cannula which protrudes from one side of the cannula casing and a passage channel running through the cannula casing and connected to the cannula. The connecting element of the catheter head has a fluid supply and is connected to the cannula casing in such a way that the fluid supply is connected to the passage channel. Furthermore, a guiding means is provided which, when the cannula casing is combined with the connecting element, guides the connecting element into the correct position onto the cannula casing. The connecting element is firmly fixed on the cannula casing by a fixing means, but can be detached again.

Such a catheter head is, for example, described in DE 299 05 068 for a subcutaneous infusion means. In this catheter head, the connecting element is plugged into the cannula casing, such that the fluid supply is arranged as an extension of the cannula. The guiding means and the fixing means is then axially symmetrical with respect to the longitudinal axis of the fluid supply. A first part of the guiding means is provided in the cannula casing as a hollow space having a circular inner wall. A second part of the guiding means is provided by an outer wall of the connecting element which during combining abuts the inner wall of the hollow space in the cannula casing. Once the cannula casing has been combined with the connecting element, the connecting element is therefore rotatably arranged in the cannula casing. A blocking mechanism is provided which fixes the connecting element in a certain angular position with respect to the casing. In each of these angular positions, however, the fluid supply forms the extension of the cannula. Different angular positions between the cannula and the fluid supply are not formed. Such a blocking mechanism is provided, for example, by a flexible sealing arm provided on the connecting element together with an exterior protrusion. Once the connecting element has been inserted into the cannula casing, the protrusion engages with a circular groove in the interior of the cannula casing and in this way fixes the connecting element to the cannula casing. In order to release the block, the flexible sealing arm is bent inwards and the connecting element can be removed from the cannula casing.

A catheter head can comprise a plate-shaped cannula casing with a cannula protruding downwards, as is known from U.S. Pat. No. 6,017,328. A connecting element, also plate-shaped, is placed onto the cannula casing in such a way that the fluid supply is arranged substantially perpendicular to the axis of the cannula. The fixing element comprises two laterally running arms which can be pressed together towards the center of the fixing element. At their ends, the arms comprise protrusions directed towards the cannula casing, via which they firmly engage with corresponding cavities on the cannula casing. The engagement can be released again by pressing the arms together. The angular position of the connecting element with respect to the cannula casing is defined by the predetermined position of the cavities on the cannula casing. The direction in which the fluid supply leads away from the cannula casing is therefore predetermined.

In the catheter heads as set forth in the prior art, it is either not possible to select an angular setting between the cannula casing or cannula and the fluid supply, or a particular angular position is pre-set and not variable. If, therefore, it is desired for the fluid to be supplied from another direction, one exemplary solution is to select a supply tube having a sufficiently large length, which can be bent to the desired other direction without disrupting the flow, or, in the case of a cannula remaining in the patient, the entire catheter head has to be rotated, which is unpleasant and unacceptable for the patient.

SUMMARY

An object of the present invention is to provide a catheter head that can be used for introducing a fluid into an organic tissue, in which a cannula casing and a connecting element can be connected to each other in a simple way and in which a variable fluid supply to the tissue is enabled.

In one embodiment, the preceding object is addressed by providing a catheter head comprising a cannula housing with a cannula, a connector element with a fluid inlet, a guide and a fixing device. The guide device has several selectable discrete rotational positions for positioning the connector element relative to the cannula housing about a longitudinal axis of the cannula. The connector element, positioned in a rotational position, is detachably connected to the cannula housing in the selected position by means of the fixing device. In general, the catheter head in accordance with the present invention may be used to introduce a fluid, for example, a medicinal fluid, into an organic tissue, but it may be used for other purposes as well.

In one embodiment, a catheter head of the type described above, for positioning the connecting element relative to the cannula casing, comprises a number of selectable, discrete rotational positions about a longitudinal axis of the cannula. The connecting element, positioned in a rotational position, is detachably fixed to the cannula casing in the selected rotational position by the fixing means. In the case of a catheter head, it is also possible to detach the fixing means, select another positioning of the connecting element relative to the cannula casing, and fix the connecting element to the cannula casing again in this rotational position, without completely separating the connecting element from the cannula casing. When fixing the connecting element to the cannula casing, the fluid supply is preferably arranged at an angle to the longitudinal axis of the cannula. Using the catheter head in accordance with the invention, it is possible to provide a fluid supply from different directions, when introducing or administering a fluid into an organic tissue. This extends a patient's freedom of movement and can ensure that the fluid is optimally introduced.

In a preferred embodiment of a catheter head in accordance with the invention, the cannula casing is formed to be substantially flat or plate-like. The casing is preferably circular in a top view. The cannula protrudes substantially perpendicular from the planar, for example, the level side facing the tissue. However, it is also conceivable to arrange the cannula at an angle to the perpendicular of the cannula casing. The cannula is preferably provided in the center of the cannula casing on this side, but can also be arranged on the edge of the cannula casing. The connecting element, also planar and preferably circular, is arranged on the opposite planar side facing away from the tissue. Once the connecting element has been fixed to the cannula casing, the fluid supply is then preferably arranged substantially perpendicular to the axis of symmetry of the cannula casing, i.e., the fluid to be introduced is diverted by about 90 degrees inside the catheter head. Depending on the requirements for introducing a fluid, however, a different angular position can also be fulfilled, or the fluid supply can be arranged in the extension of the cannula. It is then advantageous if the individual rotational positions of the guiding means can be freely selected, the fluid can then be supplied into the catheter head from any direction, adjusted to the specific requirements. When the cannula casing and the connecting element are combined, the liquid connection can, for example, be formed by a needle at the end of the fluid supply of the connecting element, which is inserted into the passage channel of the cannula casing. It is, however, also possible to provide a joint transition region in the design of the catheter head, into which both the fluid supply of the connecting element and the passage channel of the cannula casing feed.

In some preferred embodiments, a locking connection is provided for forming the various selectable discrete rotational positions between the cannula casing and the connecting element, wherein the individual locking settings correspond to the discrete rotational positions. Two locking means, adjusted to and/or complementary to each other, can, for example, be provided for this purpose. A first locking means is arranged at least on a partial region of an annular area of the cannula casing. A second locking means is arranged at least on a partial region of an annular area of the connecting element and is directed against the first locking means. The partial regions of an annular area thus correspond to a sector area along the circumference about the center, i.e., the centerpoint of the circular cannula casing or connecting element, respectively, whereby the locking means are formed on annular sector areas. The annular sector area of the first locking means on the cannula casing and the annular sector area of the second locking means on the connecting element face each other, such that the locking means can cooperate when the catheter head is combined. The annular sector areas of the locking means can then be arranged both in a region near the center, in a region away from the center, and on an outer circumference of the cannula casing or connecting element, respectively. Care merely has to be taken that the arrangements of the annular sector areas on the cannula casing and on the connecting element are adjusted to each other. When placing the cannula casing and the connecting element onto each other, these two parts can be rotated about the center against each other, until they have a desired rotational position with respect to each other. By further joining the two parts together, the connecting element is guided in this selected position along the corresponding locking setting onto the cannula casing. Accordingly, a number of selectable discrete rotational positions of the connecting element relative to the cannula casing are provided by the different locking positions of the connecting element.

In one preferred embodiment, the first and second locking means are each formed by protrusions, e.g., ribs. In some embodiments, it is possible for one of the two locking means to be formed by a number of protrusions and the other locking means to be formed by one protrusion only. In one preferred embodiment, both locking means comprise a number of protrusions. The protrusions are at least partially directed towards the center of the cannula casing or connecting element, respectively, and in particular are arranged radially orientated towards the center. When the connecting element is positioned on the cannula casing, the second protrusions of the connecting element interlock between the first protrusions of the cannula casing. The areas of the protrusions protruding from the annular sector region can be arranged obliquely with respect to the base area formed by this region, in order to enable the first and second protrusions to slide gently into each other. In this embodiment, the first and second locking means move substantially directly towards each other. It is, however, also possible to provide the first locking means on an outer circumferential area of the cannula casing, using protrusions which protrude radially outwards from the cannula casing. To this end, teeth could, for example, be provided on the edge of the cannula casing. As corresponding second locking means, protrusions which axially protrude towards the cannula casing can be provided on the outer edge on the connecting element, which engage with the intermediate spaces of the teeth on the cannula casing in order to position the connecting element.

In some embodiments, it is sufficient for the present invention if the first and second locking means are arranged on partial regions of an annular area. The locking means can also, however, be provided on the entire annular area. There further exists the possibility of forming the locking means of the cannula casing and the locking means of the connecting element on the entire annular area on one of these parts and only on a partial region of the annular area on the other part. Preferably, in some embodiments, the first locking means of the cannula casing are formed on the entire circumferential annular area and the second locking means of the connecting element are only formed on an annular sector area. This division of the locking elements enables discrete positions to be provided on the entire circumference of the catheter head which are freely selectable when positioning the connecting element on the cannula casing.

In accordance with a preferred embodiment in accordance with the present invention, the fixing means can be formed by a releasable clamping connection between the cannula casing and the connecting element. Using such a clamping connection, the connecting element—once positioned—is fixed on the cannula casing in a selected rotational position. The clamping connection is preferably formed by at least one elongated opening slit through the connecting element. At least one outer region in the connecting element is defined by the opening slit and can be moved towards the center. The outer region can, for example, be moved in this direction by a pressure directed substantially onto the center of the connecting element. This pressure can, for example, be exerted by pressing the connecting element together between thumb and forefinger. When the pressure abates, the outer region is reset again. For the clamping connection, at least a first clamping element is arranged on the cannula casing. At least a second clamping element is arranged on the outer region of the connecting element defined by the opening slit, such that—like the latter—it can be moved when the outer region is pressed together. The second clamping element is arranged on the connecting element on a side facing the cannula casing and cooperates with the first clamping element. The elongated opening slits can begin on the edge of the connecting element and terminate in its interior, whereby the outer region is divided off from the connecting element as a type of arm. The elongated opening slit can however also lie completely in the interior of the connecting element. Care merely has to be taken that the elongated opening slit runs at least partially in the circumferential direction, in order to form a movable outer region of the connecting element.

In one preferred embodiment of the present invention, the first clamping element is formed by one or more first barbs extending in the circumferential direction at least on a partial region on the cannula casing and directed towards the connecting element. Preferably, a first barb is provided which is formed in the shape of an annular sector and arranged along an annular sector on the cannula casing. It is, however, also conceivable to arrange a number of barbs, for example, rectangular barbs, adjacently on the annular sector of the cannula casing. The second clamping element is formed by one or more second barbs which are embodied complementarily to the first barbs. Preferably, a second barb is provided which extends in the circumferential direction at least on a partial region on the outer region of the connecting element and is directed towards the cannula casing. This partial region is preferably also formed as an annular sector. A number of second barbs, arranged adjacently on the annular sector, are also conceivable. Furthermore, a single, elongated hook or hook shaped annular sector can be provided on the cannula casing and, correspondingly, one or more shorter hooks on the other of the two parts. It is advantageous to provide two elongated opening slits on an opposite side of the connecting element with respect to the center, whereby two outer regions are defined, having at least one barb each. In order to fix the cannula casing to the connecting element, the outer regions of the connecting element can be pressed together via the barb, such that said second barb can engage with a complementary first barb on the cannula casing. When fixing the connecting element on the cannula casing using the fixing means, the first and second locking means of the guiding means can slide on each other. If, for example, protrusions are provided on an annular sector area of the connecting element as locking means of the guiding means, then when the outer regions are pressed together, said protrusions can slide along the complementary protrusions formed on the cannula casing when the outer region is pressed in.

Any other known or suitable clamping connection can also be used as the clamping connection of the fixing means, such as, for example, a positive lock plug connection including corresponding clamping elements on the cannula casing and on the connecting element.

In accordance with the present invention, it is also possible to provide the guiding means partially or completely on the fixing means. To this end, the function of the guiding means can, for example, be fulfilled by the first and second clamping elements of the fixing means cooperating. For example, a first locking means, such as teeth, pins or other suitable structures, can be additionally provided on the first clamping element and a second locking means, such as complementary teeth, holes or other suitable structures for the pins, can be additionally provided on the second clamping element. In this way, a particular locking setting can be selected as a discrete rotational position at the same time as the connecting element is fixed to the cannula casing.

By arranging the elements of the guiding and fixing means rotationally symmetrically about the center of the cannula casing or connecting element, respectively, the connecting element can be moved into a particular rotational position relative to the cannula casing, wherein due to their rotational symmetry, the respective complementary first and second locking and clamping elements oppose each other in a mutual fit and can cooperate in each rotational position.

DETAILED DESCRIPTION

Figure 1:
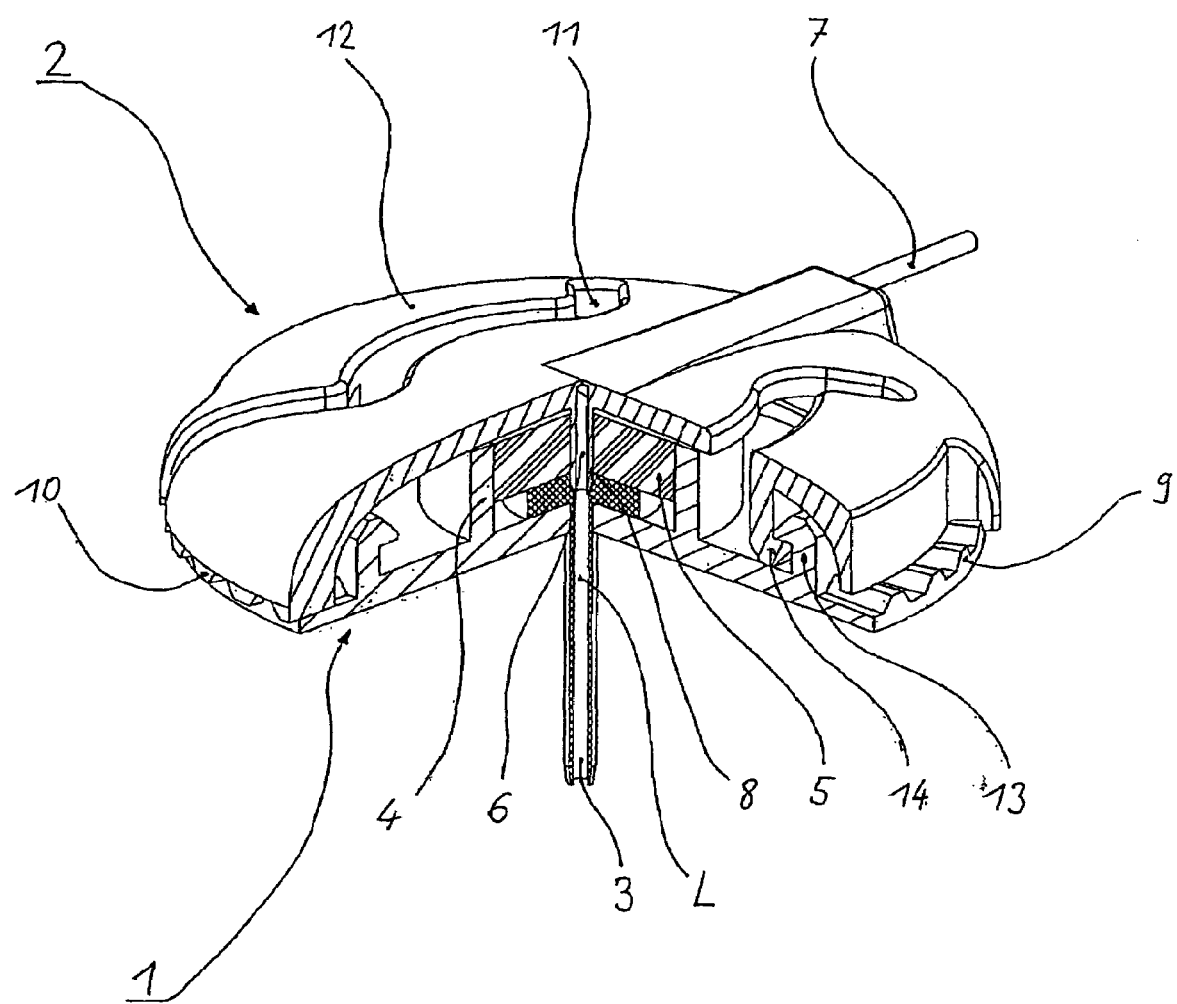
FIG. 1 is a perspective view, including a partial section through a catheter head in accordance with one embodiment of the present invention.

FIG. 1 shows a catheter head in accordance with one embodiment of the present invention, comprising a circular, flat cannula casing 1 and a circular, flat connecting element 2 fixed to said cannula casing 1. A cannula 3 protrudes from the cannula casing 1, and in the drawing is directed substantially downwards, perpendicularly from the cannula casing 1. The cannula 3 can, however, protrude from the cannula casing 1 at any other angle and therefore penetrate organic tissue at any angle. In the example shown, a wall 4 which is arranged annularly about a central opening protrudes upwards from the cannula casing 1. The cannula 3 is guided though the central opening and secured by an insertion part 5, i.e. a septum, inserted within the circumference of the wall 4. The septum 5 also comprises a central opening which forms the passage channel 6.

The connecting element 2 comprises a fluid supply 7 which feeds into a tube-like central continuation 8 arranged centrally in the middle of the connecting element 2. The continuation 8 is guided along the central opening of the septum 5 until it feeds into the cannula 3, whereby a liquid connection from a fluid container (not shown, but typical) via the fluid supply 7 and the cannula 3 into the organic tissue is established. If the connecting element 2 is only partially inserted into the central opening of the septum 5, it can be rotated about the axis of the tube-like continuation 8—which at the same time also represents the extension of the longitudinal axis of the cannula—relative to the cannula casing.

In the example shown in FIG. 1, the guiding means is formed in accordance with the present invention by first protrusions 9 on the cannula casing 1 and by second protrusions 10 on the connecting element 2. The protrusions 9 are arranged on an outer annular area of the cannula casing 1 which points upwards, wherein the first protrusions on said annular area extend or are aligned generally radially with respect to the center of the cannula casing. The second protrusions 10 of the connecting element 2 are arranged on the circumferential edge area of the connecting element 2, wherein the edge of the connecting element 2 with the second protrusions 10 is curved towards the cannula casing 1 in such a way that the second protrusions 10 are arranged generally opposite the first protrusions 9. The second protrusions 10 therefore also run, extend or are aligned generally radially towards the center of the cannula casing 1 or connecting element 2, respectively.

When placing the connecting element 2 onto the cannula casing 1, i.e., when inserting the continuation 8 into the central opening of the insertion part 5, the connecting element 2 can be rotated relative to the cannula casing 1, until the fluid supply 7 is led away from the catheter head in a desired direction. This selected position either directly corresponds to one of the discrete rotational positions of the guiding means or can be moved into a nearby position corresponding to a discrete rotational position by a slight, negligible angular movement. This discrete rotational position is determined by the second protrusions 10 on the connecting element 2 engaging with the intermediate space, opposite in this position, between the first protrusions 9 on the cannula casing 1. When the connecting element 2 and the cannula casing 1 are further joined together, these two parts are guided by the protrusions 9 and 10 which slide into each other. In order to enable the discrete positions to be located and the continuation 8 to be gently inserted, the protruding sides of the protrusions are arranged obliquely with respect to their base area. The connecting element 2 is inserted into the cannula casing 1 until the second protrusions 10 rest on the base area of the intermediate spaces of the first protrusions 9. In this state, the continuation 8 protrudes into the cannula 3 to a certain depth, in order to ensure the fluid connection. If a different rotational position of the connecting element 2 relative to the cannula casing 1 is desired, the connecting element 2 is raised slightly from the cannula casing 1, until the engagement between the protrusions 9 and 10 is released. The connecting element 2 can then be rotated again relative to the cannula casing 1, until a desired new rotational position has been reached. By pushing the connecting element 2 and the cannula casing 1 together, the second protrusions 10 of the connecting element 2 are then inserted into the intermediate space between the first protrusions 10 of the cannula casing 1, now opposite them in accordance with the new discrete rotational position. When the connecting element 2 is raised from the cannula casing 1 in order to change a rotational position, the continuation 8 preferably remains in the central opening of the septum 5, preferably in the cannula 3, at least via its tip, in order to not interrupt the fluid connection despite the change in rotational position.

In order to form the fixing means, two elongated opening slits 11 through the connecting element 2 are arranged in accordance with the invention in the example shown in FIG. 1. The slits begin from the edge of the connecting element 2 and initially run substantially towards the center of the connecting element 2, then pass into a part running substantially in the circumferential direction, and terminate in a part running substantially radially outwards again before the edge of the connecting element 2. Accordingly, they are formed in generally curved or wave shape. Two outer regions 12 of the connecting element 2 are defined by these opening slits 11. The outer regions each form a sort of arm of the connecting element 2, which can be moved towards the center of the connecting element 2 if a pressure is exerted on the outer regions from the edge.

A first barb 13 is provided on the cannula casing 1, as a first clamping element of the fixing means, and protrudes upwards from the cannula casing 1 towards the connecting element 2. The first barb 13 is preferably formed by a projection protruding towards the center of the cannula casing 1 and is circumferentially arranged on the entire circumference of the cannula casing 1, annular about the center of the cannula casing 1. It is, however, also possible to only arrange the barb on circumferential sectors. On the connecting element 2, second barbs 14 protruding downwards towards the cannula casing 1, complementary to the first barb 13, are arranged on the outer regions 12, as second clamping elements of the fixing means. The barbs 14 extend in the circumferential direction on the edge of the part of the opening slits 11 running in the circumferential direction. The second barbs 14 can run continuously along the part of the opening slit 11 running in the circumferential direction or can be interrupted.

When placing the connecting element 2 onto the cannula casing 1, the outer regions 12 of the connecting element 2 are pressed together, e.g., by the thumb and forefinger, such that the second barbs 14 move towards the center of the connecting element 2 and, when the connecting element 2 is inserted into the cannula casing 1, are guided past the first barb 13 of the cannula casing 1. Preferably, the outer regions 12 can be moved far enough inside that the second barbs 14 do not rub on the first barb 13.

If a rotational position has been selected and the cannula casing 1 and the connecting element 2 guided completely into each other in said rotational position, the pressure on the outer regions 12 is reduced and the barbs 13 and 14 interlock into each other in a clamping connection. If a new rotational position is to be selected, the outer regions 12 are pressed together again, in order to release the clamping connection of the barbs 13 and 14, such that the connecting element 2 can be at least partially raised from the cannula casing 1, at least until the locking connection of the guiding means is released. The connecting element 2 and the cannula casing 1 can then be rotated relative to each other, into a new desired rotational position. By pushing the cannula casing and the connecting element completely together when the outer regions 12 are pressed in, the second protrusions 10 can in turn engage with the intermediate spaces between the first protrusions 9, corresponding to the new rotational position. By abating, reducing, or relieving the pressure on the outer regions 12, the barbs 13 and 14 interlock into each other and the connecting element 2 is fixed on the cannula casing 1 in this new discrete rotational position.

In the exemplary embodiments shown in FIG. 1, the first protrusions 9 are provided on the entire circumferential area of the cannula casing 1, whereas the second protrusions 10 of the connecting element 2 are only provided on the edge of the regions between the movable outer regions, i.e., second protrusions 10 are not provided on the edge of the outer regions in the example shown. This facilitates the engaging of the clamping elements 13 and 14. It would, however, be equally possible to also attach second protrusions 10 to the edge of the outer regions 12. These second protrusions 10 would then slide along the first protrusions 9 when the clamping elements 13 and 14 engage and the pressure on the outer regions 12 is abated.

It is also conceivable to provide the first and second, mutually complementary locking elements of the guiding means on the mutually facing areas of the clamping elements 13 and 14. To this end, corresponding cooperating protrusions could, for example, be provided on the projections of the barbs 13 and 14. In this case, the guiding means and the fixing means would be combined into one means.

Figure 2:
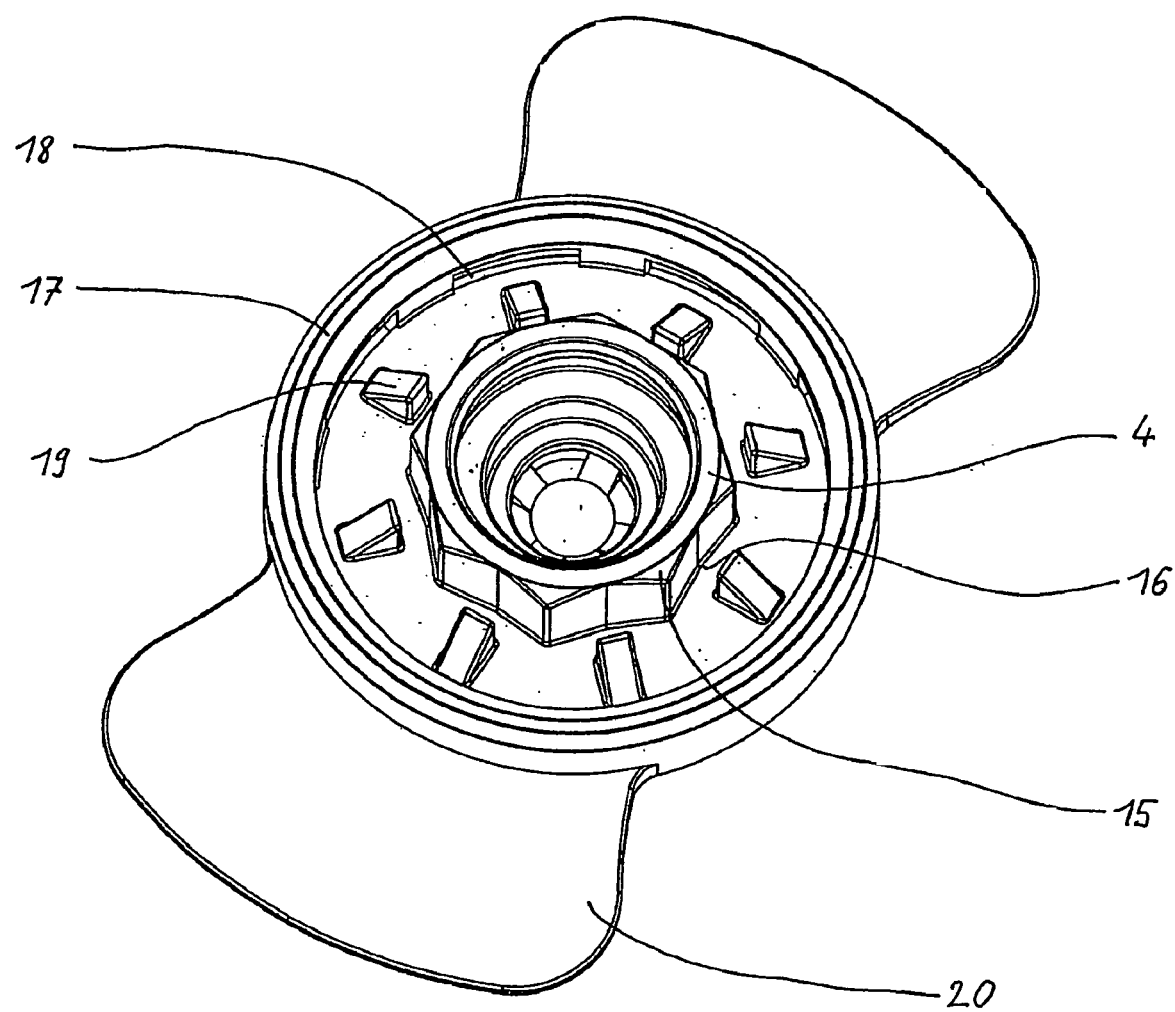
FIG. 2 is a perspective view of a cannula casing in accordance with another embodiment of the present invention.

FIG. 2 shows a cannula casing 1 of another exemplary embodiment of a catheter head in accordance with the present invention, which is also formed circularly and from which a cannula protrudes downwards (not visible in FIG. 2). In this embodiment, the guiding means in accordance with the present invention is provided on the wall 4 arranged around the central opening. In order to form a locking connection between the cannula casing 1 and a connecting element, to provide the discrete rotational positions in accordance with the invention, protrusions 15—preferably triangular—are provided on the wall 4, generally in the circumferential direction around the wall. Through these triangular protrusions 15, the outer circumference of the wall 4 is formed in a sort of star shape. It is then possible for adjacent wall areas of adjacent triangles to be orientated in the same direction and therefore to form a joint area, or for a recess to be created between adjacent triangles when the adjacent areas of these triangles are at an angle with respect to each other. Furthermore, the protrusions 15 provided on the wall 4 do not have to be formed triangularly, but can, for example, also be quadrangular, can be formed by curves or can have any other suitable configuration.

The discrete rotational positions are provided by the protrusions 15 formed on the circumferential area of the wall 4, by an intermediate space 16 between two protrusions 15, which is formed, for example, by adjacent wall areas of adjacent triangular protrusions 15, corresponding to a discrete rotational position. The number of discrete rotational positions of a catheter head in accordance with the present invention can be varied by varying the number of protrusions on the wall 4.

On the connecting element corresponding to the cannula casing 1 of an embodiment as set forth in FIG. 2, a wall can be provided around the continuation 8, the wall protruding from the connecting element towards the cannula casing 1. Protrusions can be provided on an inner circumferential area of the wall which run complementarily to the protrusions 15 of the cannula casing 1. In case intermediate spaces 16 are formed by the protrusions 15 on the outer circumferential area of the wall 4 of the cannula casing 1, as shown in FIG. 2, the protrusions on the inner circumferential area of the wall of the connecting element are formed in such a way that they fit into said intermediate spaces 16. To this end, triangular protrusions having an obtuse angle can, for example, be provided. If adjacent areas of adjacent protrusions 15 on the wall 4 of the cannula casing 1 form a joint area, the inner circumferential area of the wall of the connecting element is formed as a polygon having inner areas corresponding or complementary to the joint areas of the protrusions 15. If the protrusions 15 on the outer circumferential area of the wall 4 are provided by curves, then curves can also be formed on the inner circumferential area of the wall of the connecting element, said curves fitting into the intermediate spaces 16.

In the embodiment depicted in FIG. 2, the fixing means for a releasable clamping connection comprises an annularly circumferential elevation 17 on an outer region of the cannula casing 1. A number of elongated recesses 18 running in the circumferential direction are provided in the inner circumferential area of the elevation 17. On a connecting element corresponding to this fixing means, clamping elements on the movable outer regions 12 can be provided with a protrusion which fits into the recesses 18.

A discrete rotational position is selected for the catheter head and the clamping connection between the cannula casing and the connecting element is established analogously to the embodiment described with reference to FIG. 1. In order to facilitate removing the connecting element 2 by pressing the outer regions 12 together and raising it off the cannula casing 1, guiding blocks 19 for the clamping elements are provided in front of the recesses 18 on the base area of the cannula casing 1. Preferably, the recesses 18 and the intermediate spaces 16 are arranged opposite each other and the guiding blocks 19 are arranged between the recess 18 and the intermediate spaces 16. The guiding blocks 19 are preferably formed as wedge-shaped ramps, such that they comprise a guiding area which rises in the radial direction from the edge of the cannula casing 1. A clamping element of the connecting element, when raised by pressing the biased outer regions 12 together, is repelled upwards from the cannula casing, along said guiding area.

On or adjacent to the edge of the cannula casing 1, flaps 20 are provided on opposite sides and serve, for example, to hold the cannula casing 1 on the surface of the tissue when the connecting element is raised.

The embodiments shown in the drawings are to be understood to be exemplary and are not intended to restrict the scope of the invention. In particular, the angular arrangement of the cannula 3 and the fluid supply 7 of the catheter head in accordance with the present invention can be altered.

In the foregoing description, embodiments of the present invention, including preferred embodiments, have been presented for the purpose of illustration and description. They are not intended to be exhaustive or to limit the invention to the precise forms disclosed. Obvious modifications or variations are possible in light of the above teachings. The embodiments were chosen and described to provide the best illustration of the principals of the invention, methods of making the invention, and the practical application and use of the invention, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A catheter head for introducing a fluid into an organic tissue, said catheter head comprising:
   a) a cannula casing comprising a cannula protruding on one side of said cannula casing and a passage channel running through the cannula casing and connected to said cannula;
   b) a connecting element which includes a fluid supply and can be connected to the cannula casing in such a way that said fluid supply is fluidly connected to said passage channel;
   c) guide formed jointly by the cannula casing and said connecting element, for positioning and guiding the connecting element relative to the cannula casing;
   d) a fixing means for detachably fixing the connecting element to the cannula casing; positioned in a rotational position, to the cannula casing in said selected rotational position, wherein the fixing mechanism forms a releasable clamping connection between the cannula casing and the connecting element; wherein said guide exhibits a plurality of selectable, discrete rotational positions about the longitudinal axis of the cannula;
   e) said passage channel of said cannula casing and said fluid supply of said connecting element are configured such that they are fluidly connected to each other at each of the plurality of selectable, discrete rotational positions; and
   f) the clamping connection is formed by:
   at least one elongated opening slit through the connecting element, by which at least one outer region is formed in the connecting element which can be moved towards a center of the connecting element;

at least one first clamping element which is arranged on the cannula casing and which includes at least one first barb extending in a circumferential direction at least on a partial region on the cannula casing and directed towards the connecting element;

and at least one second clamping element which is arranged on the connecting element and which includes at least one second barb, complementary to said first barb, which extends in the circumferential direction at least on a partial region on the outer region of the connecting element and is directed towards the cannula casing and which engages with the first barb to fix the cannula casing to the connecting element.

2. The catheter head as set forth in claim 1, wherein once the connecting element has been fixed to the cannula casing, the fluid supply is arranged at an angle to said longitudinal axis of the cannula.

3. The catheter head as set forth in claim 1, wherein the cannula protrudes substantially perpendicularly from the cannula casing and the fluid supply, once fixed, is arranged substantially perpendicular to the cannula.

4. The catheter head as set forth in claim 1, wherein the rotational positions of the guide can be freely selected.

5. The catheter head as set forth in claim 1, wherein the guide forms a locking connection between the cannula casing and the connecting element for said selectable, discrete rotational positions.

6. The catheter head as set forth in claim 5, wherein said locking connection is formed by:

a first locking mechanism which is provided at least on a partial region of an annular area of the cannula casing; and a second locking mechanism directed against said first locking mechanism which is provided at least on a partial region of an annular area of the connecting element facing said partial region of said annular area of the cannula casing and which cooperates with the first locking mechanism when the connecting element is positioned.

7. The catheter head as set forth in claim 6, wherein the first locking mechanism is formed by first protrusions and the second locking mechanism is formed by second protrusions, said second protrusions on the connecting element engaging between the first protrusions on the cannula casing when the connecting element is positioned.

8. The catheter head as set forth in claim 6, wherein the first and second locking mechanisms slide on each other when the connecting element is fixed to the cannula casing.

9. The catheter head as set forth in claim 1, wherein the guide is provided by first and second clamping elements of the fixing mechanism cooperating.

10. The catheter head as set forth in claim 1, wherein the locking connection of the guide is formed by first and second locking mechanism which are provided on the first and second clamping elements and cooperate.

11. The catheter head as set forth in claim 1, wherein the guide is provided partially or completely on the fixing mechanism.

12. The catheter head as set forth in claim 1, wherein the first and second locking mechanisms slide on each other when said at least one outer region of the connecting element is pressed in towards the center of the connecting element.

* * * * *